(12) United States Patent
Sakai et al.

(10) Patent No.: US 12,702,472 B2
(45) Date of Patent: Aug. 11, 2026

(54) CAUTERY PUNCTURE NEEDLE

(71) Applicants: YOKOWO CO., LTD., Tokyo (JP); FUKUDA DENSHI CO., LTD., Tokyo (JP)

(72) Inventors: Koichi Sakai, Tokyo (JP); Junya Maeda, Tokyo (JP); Mineta Suzuki, Tokyo (JP); Yasuhiro Shirakawa, Tokyo (JP)

(73) Assignees: YOKOWO CO., LTD., Tokyo (JP); FUKUDA DENSHI CO., LTD., Tokyo (JP)

( * ) Notice: Subject to any disclaimer, the term of this patent is extended or adjusted under 35 U.S.C. 154(b) by 245 days.

(21) Appl. No.: 18/549,973

(22) PCT Filed: May 17, 2021

(86) PCT No.: PCT/JP2021/018532

§ 371 (c)(1),
(2) Date: Sep. 11, 2023

(87) PCT Pub. No.: WO2022/190400

PCT Pub. Date: Sep. 15, 2022

(65) Prior Publication Data

US 2024/0293172 A1 Sep. 5, 2024

Related U.S. Application Data

(60) Provisional application No. 63/159,549, filed on Mar. 11, 2021.

(51) Int. Cl.
*A61B 18/14* (2006.01)
*A61B 17/00* (2006.01)
*A61B 18/00* (2006.01)

(52) U.S. Cl.
CPC *A61B 18/1477* (2013.01); *A61B 2017/00331* (2013.01); *A61B 2018/00107* (2013.01);
(Continued)

(58) Field of Classification Search
CPC A61B 2018/00107; A61B 2018/00351; A61B 2018/00577; A61B 2018/00595;
(Continued)

(56) References Cited

U.S. PATENT DOCUMENTS 5,215,540 A * 6/1993 Anderhub ......... A61M 25/0041 604/264
5,549,581 A * 8/1996 Lurie ............... A61M 25/0054 600/374

(Continued)

FOREIGN PATENT DOCUMENTS

EP 1014870 5/2007
JP 2002500530 A 1/2002

(Continued)

OTHER PUBLICATIONS

International Search Report (with English translation) and Written Opinion issued in PCT/JP2021/018532, dated Jul. 20, 2021, 11 pages provided.

*Primary Examiner* — Bradford C. Blaise
(74) *Attorney, Agent, or Firm* — HSML P.C.

(57) ABSTRACT

A cautery puncture needle includes a pipe portion. The pipe portion has a first bent portion located on a distal end side of the pipe portion and a second bent portion located on a proximal end side of the pipe portion. A curvature radius of an arc of the first bent portion is equal to or larger than a curvature radius of an arc of the second bent portion and a length of the arc of the first bent portion is longer than a length of the arc of the second bent portion, or the length of the arc of the first bent portion is equal to or longer than the
(Continued)

length of the arc of the second bent portion and the curvature radius of the arc of the first bent portion is larger than the curvature radius of the arc of the second bent portion.

20 Claims, 7 Drawing Sheets

(52) U.S. Cl.
CPC ............... *A61B 2018/00351* (2013.01); *A61B 2018/00595* (2013.01); *A61B 2018/1417* (2013.01); *A61B 18/1492* (2013.01)

(58) Field of Classification Search
CPC .... A61B 2018/1417; A61B 2018/1425; A61B 18/1477; A61B 18/1492; A61B 2017/00292; A61B 2017/003; A61B 2017/00305; A61B 2017/00314; A61B 2017/00331; A61M 2025/0004; A61M 25/0054
See application file for complete search history.

(56) References Cited

U.S. PATENT DOCUMENTS 5,908,381 A 6/1999 Aznoian et al.
5,921,915 A 7/1999 Aznoian et al.
6,926,669 B1 8/2005 Stewart et al.
8,012,143 B1 * 9/2011 Kampa ............. A61M 25/0041 604/525
2005/0273006 A1 12/2005 Stewart et al.
2010/0130996 A1 * 5/2010 Doud .................... A61M 39/02 606/159
2010/0191315 A1 * 7/2010 Bowe ................ A61M 25/0026 607/122
2011/0184378 A1 7/2011 Kobayashi et al.
2015/0045776 A1 * 2/2015 Haac ................. A61M 25/0108 604/528
2016/0367314 A1 12/2016 Dougherty et al.
2018/0147005 A1 5/2018 Goshgarian et al.
2023/0149662 A1 * 5/2023 Kuboki ................. A61M 25/01 604/528

FOREIGN PATENT DOCUMENTS

JP 2013220202 A 10/2013
JP 2015-119829 7/2015

* cited by examiner

CAUTERY PUNCTURE NEEDLE

TECHNICAL FIELD

The present disclosure relates to a cautery puncture needle.

BACKGROUND ART

A puncture needle having two bent portions is proposed in the related art, as in Patent Literature 1.

CITATION LIST

Patent Literature

Patent Literature 1: Japanese Unexamined Patent Application Publication No. 2013-220202

SUMMARY OF INVENTION

Technical Problem

However, a user such as a doctor needs expert skill to adjust the degree of bending of the puncture needle.

Accordingly, an object of the present disclosure is to facilitate fine adjustment of degree of bending of a cautery puncture needle.

Solution to Problem

A cautery puncture needle according to an aspect of the present disclosure includes a pipe portion, and a distal end electrode portion provided at a distal end of the pipe portion and configured to allow a high-frequency current to flow. The pipe portion has a first bent portion and a second bent portion. The first bent portion is located on a distal end side of the pipe portion. The second bent portion is located on a proximal end side of the pipe portion. The first bent portion and the second bent portion are configured such that a curvature radius of an arc of the first bent portion is equal to or larger than a curvature radius of an arc of the second bent portion, and a length of the arc of the first bent portion is longer than a length of the arc of the second bent portion. Or, the first bent portion and the second bent portion are configured such that the length of the arc of the first bent portion equal to or longer than the length of the arc of the second bent portion, and the curvature radius of the arc of the first bent portion is larger than the curvature radius of the arc of the second bent portion.

Advantageous Effects of Invention

According to the present disclosure described above, degree of bending of a cautery puncture needle can be finely adjusted easily.

DESCRIPTION OF EMBODIMENTS

Hereinafter, an embodiment will be described with reference to the drawings (see FIGS. 1 to 6). Embodiments are not limited to the following embodiment. Contents described in one embodiment are similarly applied to another embodiment in principle. Embodiments and modifications may be combined as appropriate.

Figure 2:
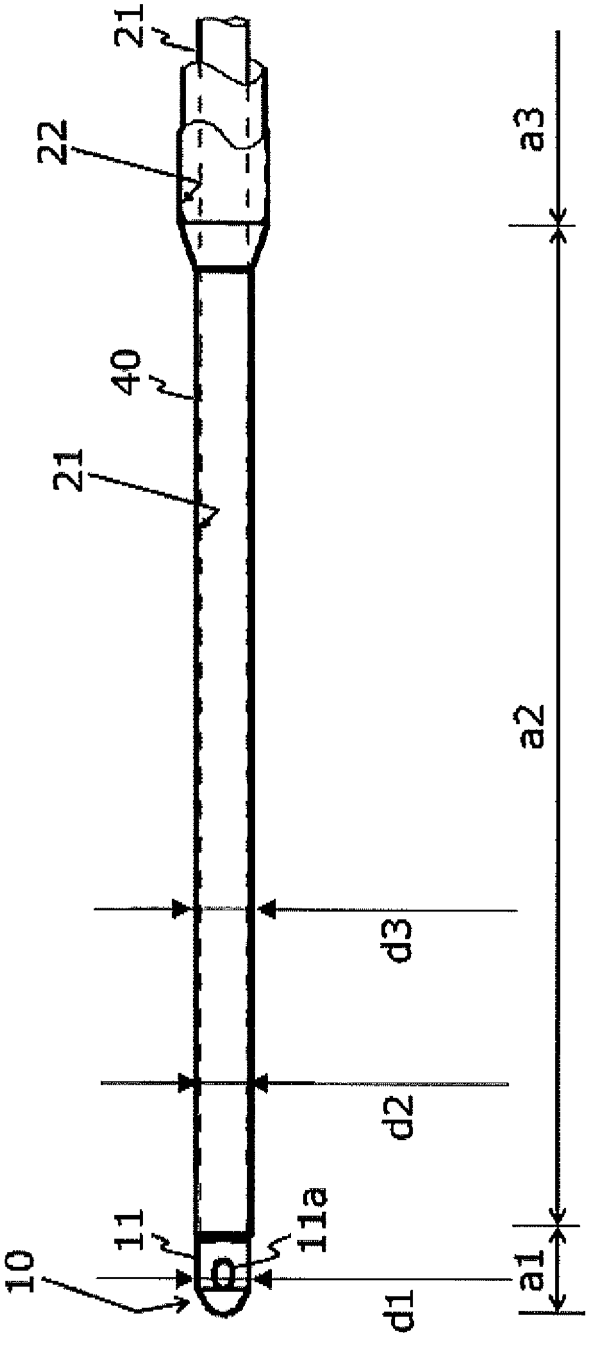
FIG. 2 is an enlarged side view of a region including a first region and a second region of the cautery puncture needle according to the present embodiment.
Figure 3:
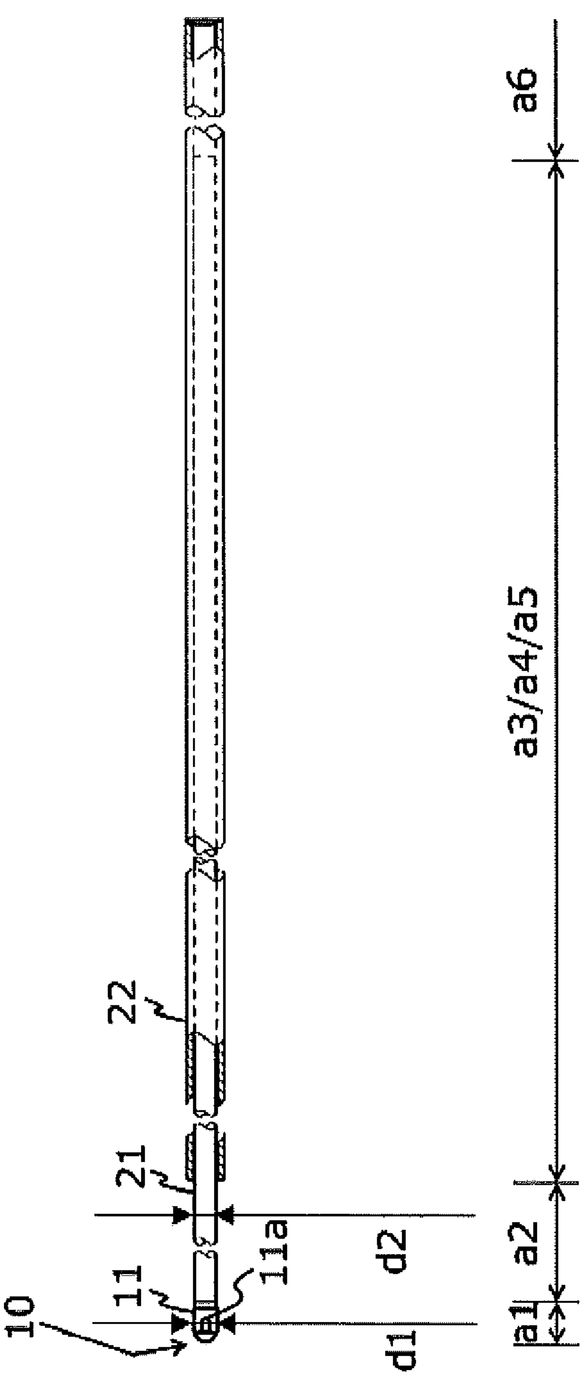
FIG. 3 shows side surfaces and partial cross sections of a distal end electrode portion, a first pipe, and a second pipe before being bent.
Figure 5:
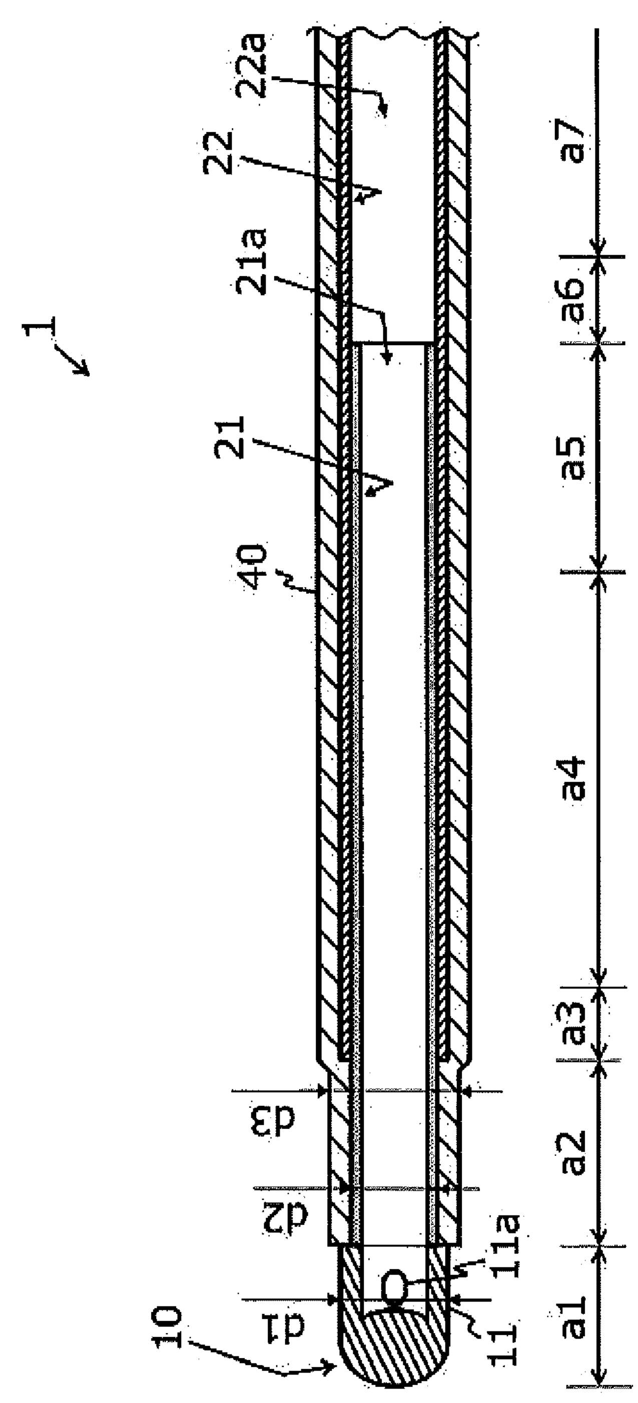
FIG. 5 shows a cross-sectional structure of the cautery puncture needle before being bent.

In FIG. 2, a first pipe 21 and a second pipe 22 hidden by a covering portion 40 to be not visible from outside are indicated by broken lines to show an internal structure of the first pipe 21 and the like. In FIG. 3, the first pipe 21 hidden by the second pipe 22 to be not visible from outside is indicated by broken lines to show the internal structure of the first pipe 21. FIG. 5 shows a first region a1 to a seventh region a7 by shortening a longitudinal direction of the second region a2 to the seventh region a7, in order to show the internal structure of the first pipe 21 and the like.

(Configuration of Cautery Puncture Needle 1)

Figure 1:
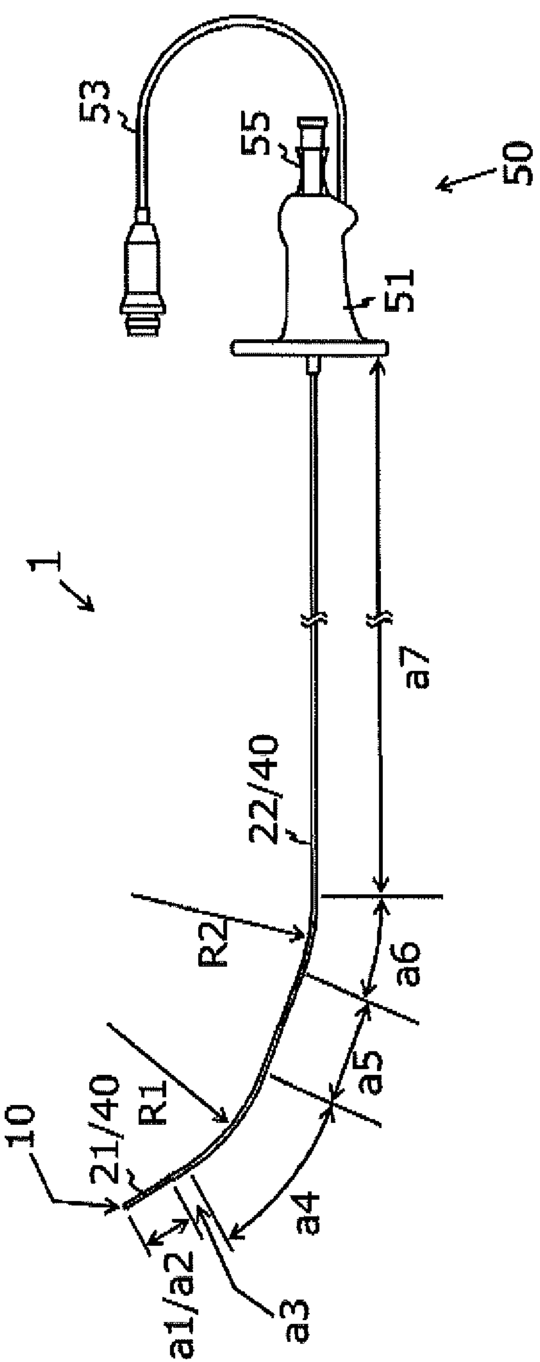
FIG. 1 is a side view of a cautery puncture needle and an operation portion according to an embodiment.

As shown in FIG. 1, the cautery puncture needle 1 according to the present embodiment includes a distal end electrode portion 10, a pipe portion (the first pipe 21, the second pipe 22), and the covering portion 40. The cautery puncture needle 1 has a proximal end side attached to an operation portion 50 such as a luer connecter 51 and the like. The cautery puncture needle 1 is used for catheter ablation (myocardial ablation) and the like, in which a high-frequency current is applied to an abnormal part in a body to cauterize the part. In the present embodiment, the first pipe 21 and the second pipe 22 are not visible from outside since the first pipe 21 and the second pipe 22 are covered with the non-transparent covering portion 40. However, the covering portion 40 may not be non-transparent but may be transparent.

(Distal End Electrode Portion 10)

As shown in FIG. 2, the distal end electrode portion 10 is provided on a distal end side of the first pipe 21. The distal end electrode portion 10 is integrally formed with the first pipe 21 by arc welding such as plasma welding and tig (Tungsten Inert Gas) welding. The distal end electrode portion 10 generates Joule heat when being supplied with a high-frequency current. A distal end of the distal end electrode portion 10 for insertion preferably has a semi-elliptical spherical shape (a cannonball shape, a shape obtained by cutting a rugby ball into two equal parts in the center in a longitudinal direction) whose outer diameter gradually decreases toward a distal end side. The shape of the distal end of the distal end electrode portion 10 for insertion is not limited thereto, and may be, for example, a hemispherical shape. The distal end electrode portion 10 is provided with, on a proximal end side thereof, a tube portion 11 communicating with the first pipe 21. The tube portion 11 is formed with a hole 11*a*. The hole 11*a* is used as an ejection hole for ejecting a contrast agent. The hole 11*a* is formed by laser processing and the like.

The distal end electrode portion 10 is made of metal to pass a high-frequency current. The distal end electrode portion 10 is preferably made of a metal that can be imaged with high contrast by X-ray fluoroscopy, for example, platinum, iridium, an alloy of platinum and iridium, an alloy of platinum, iridium and stainless steel, so that a position of the distal end electrode portion 10 in a surgical site can be easily confirmed.

In the present embodiment, the tube portion 11 is provided on the proximal end side of the distal end electrode portion 10. Alternatively, the tube portion 11 may also be provided on a distal end side of the first pipe 21.

(First Pipe 21)

Figure 4:
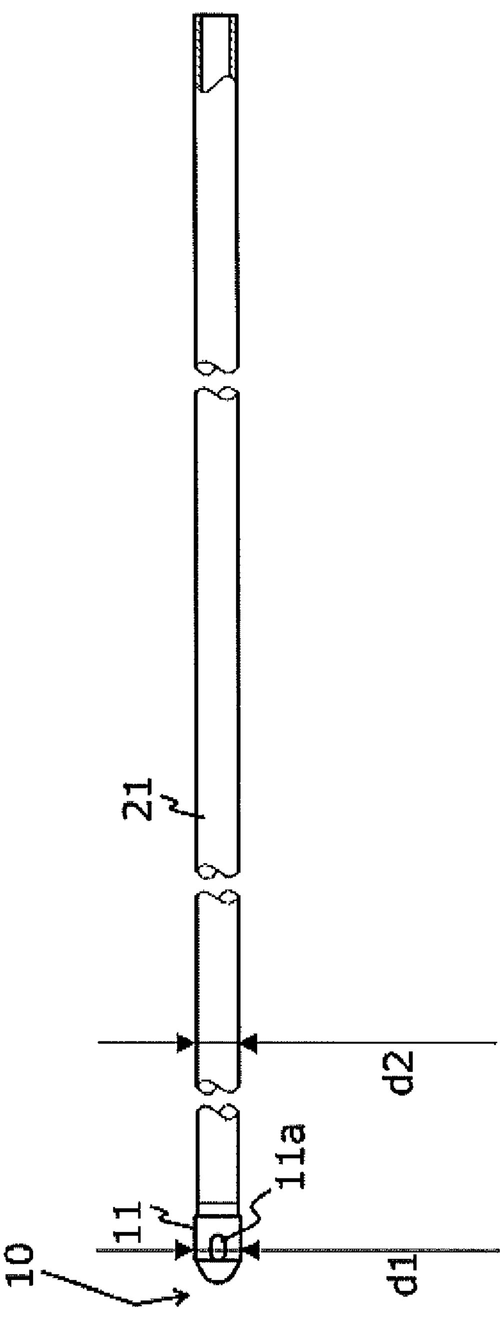
FIG. 4 shows side surfaces and partial cross sections of the distal end electrode portion and the first pipe.

As shown in FIGS. 3 and 4, the first pipe 21 is a hollow cylindrical pipe. The first pipe 21 communicates with the tube portion 11 of the distal end electrode portion 10 on the distal end side, and communicates with the second pipe 22 on a proximal end side. That is, the distal end electrode portion 10 is provided on the distal end side of the first pipe 21. The first pipe 21 extends from a region in contact with the distal end electrode portion 10 to a region in the vicinity of a terminal end portion of the second pipe 22 on a proximal end side in a linear region through inside of the second pipe 22 (the second region a2 to the fifth region a5 described later).

A region of an outer side surface of the first pipe 21 on the distal end side that is not inserted into the second pipe 22 is subjected to a satin like surface treatment by blasting and the like. Specifically, an entire region of the outer side surface of the first pipe 21 covered with the covering portion 40 described later is subjected to the satin like surface treatment. The first pipe 21 is made of a metal having good flexibility, for example, stainless steel such as SUS 302, SUS 304V, and SUS 316L, or various alloys such as nitinol and CoCr.

(Second Pipe 22)

As shown in FIG. 5, the second pipe 22 is a hollow cylindrical pipe. The second pipe 22 has an inner diameter equal to or slightly larger than an outer diameter of the first pipe 21. The second pipe 22 communicates with the first pipe 21 on a distal end side and communicates with the operation portion 50 on a proximal end side. The second pipe 22 extends from a region near the distal end electrode portion 10 to a region where the operation portion 50 is provided (the third region a3 to the seventh region a7 described later).

An outer side surface of the second pipe 22 is subjected to a satin like surface treatment by blasting or the like. Specifically, an entire region of the outer side surface of the second pipe 22 covered with the covering portion 40 described later is subjected to the satin like surface treatment. The second pipe 22 is made of a metal having good flexibility, for example, stainless steel such as SUS 302, SUS 304V, and SUS 316L, or various alloys such as nitinol and CoCr.

The first pipe 21 is inserted into the second pipe 22 from the distal end side of the second pipe 22. The first pipe 21 and the second pipe 22 are joined by laser welding, adhesion, and the like to form the pipe portion. In the pipe portion, a distal end side (the second region a2) is implemented by a single layer that is the first pipe 21, a proximal end side (the sixth region a6 and the seventh region a7) is implemented by a single layer that is the second pipe 22, and a portion between the distal end side and the proximal end side (the third region a3 to the fifth region a5) is implemented by two layers including the first pipe 21 and the second pipe 22.

(Grain Size of Grindstone for Blasting)

The grain size of the grindstone used for blasting the first pipe 21 and the second pipe 22 is preferably set at substantially mesh 80 (grain size that passes through a sieve divided into 80 parts per square inch and does not pass through a sieve divided into 100 parts per square inch) in accordance with grain size JIS. The grain size of the grindstone used for blasting is not limited to mesh 80.

(Covering Portion 40)

A region of the outer side surface of the first pipe 21 on the distal end side that is not inserted into the second pipe 22, and the outer side surface of the second pipe 22 are covered with the covering portion 40. The covering portion 40 is used to prevent unintended high-frequency cauterization to a blood vessel, an organ, and the like, and to reduce the sliding resistance of the cautery puncture needle 1 in a living body. The covering portion 40 is made of a hydrophobic resin material, for example, a fluorine-based resin including PTFE (polytetrafluoroethylene), ETFE (tetrafluoroethylene-ethylene copolymer), and PFA (tetrafluoroethylene-perfluoroalkyl vinyl ether copolymer). The covering portion 40 is a heat-shrinkable tube, and is shrunk by heating after a pipe (the first pipe 21 and the second pipe 22) is inserted into the heat-shrinkable tube to be brought into close contact with the pipe.

(Operation Portion 50)

The operation portion 50 on the proximal end side of the second pipe 22 includes the luer connecter 51, a relay cable 53, and a syringe connection portion 55 (see FIG. 1). The relay cable 53 electrically connects a source of a high-frequency (radio wave (RF)) current, the second pipe 22, the first pipe 21, and the distal end electrode portion 10. The syringe connection portion 55 is a luer taper fitting portion to which a syringe is connected. By connecting a syringe filled with a contrast agent to the syringe connection portion 55 and injecting the contrast agent into a first hollow portion 21*a* and a second hollow portion 22*a*, the contrast agent is ejected to outside from the hole 11*a* formed in the tube portion 11 of the distal end electrode portion 10 (see FIG. 5).

(Outer Diameters of Portions)

The distal end electrode portion 10, the first pipe 21, and the covering portion 40 are configured such that the distal end electrode portion 10 has an outer diameter d1 larger than an outer diameter d2 of the first pipe 21, and smaller than an outer diameter d3 of the covering portion 40 in a region in which the covering portion 40 covers the first pipe 21 (see FIGS. 2 to 5, for example, d1=0.75 mm, d2=0.70 mm, and d3=0.83 mm). That is, a relation of $d2<d1<d3$ is established. Here, the outer diameter d1 of the distal end electrode portion 10 is defined as the outer diameter of a part having a largest outer diameter between a proximal end side part having a semi-elliptical spherical shape or a hemispherical shape and the tube portion 11.

(Configuration of Bent Portions)

Figure 6:
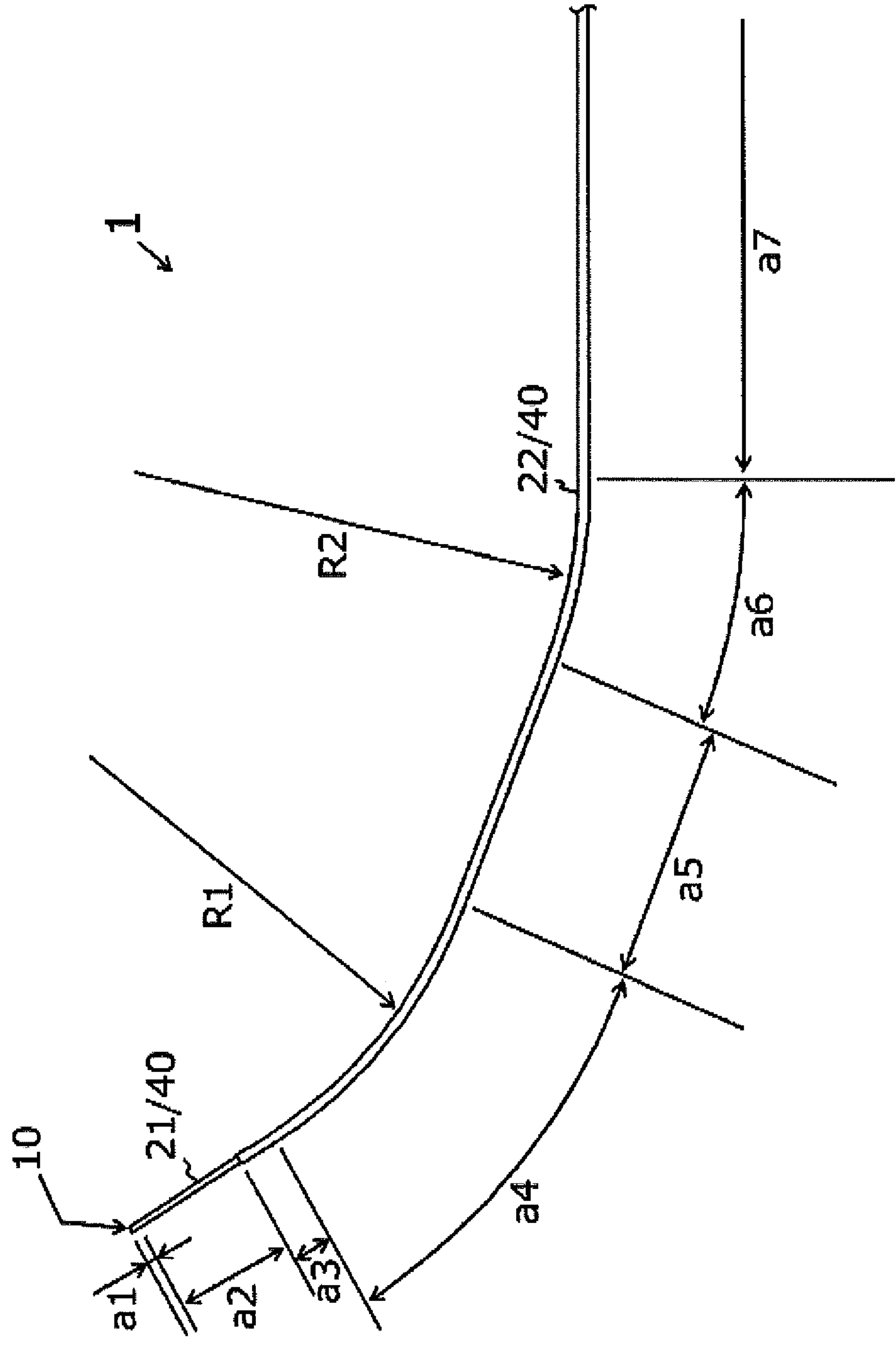
FIG. 6 is an enlarged side view of the cautery puncture needle according to the present embodiment.

The cautery puncture needle 1 has two bent portions between the distal end electrode portion 10 and the proximal end side of the second pipe 22 (see FIGS. 1 and 6). The two bent portions are formed by bending corresponding areas (the fourth region a4 and the sixth region a6) where the pipe portion (the first pipe 21 and the second pipe 22) formed in a substantially linear shape and covered with the covering portion 40.

The bent portions are formed after the distal end electrode portion 10 is attached to the first pipe 21, the first pipe 21 is attached to the second pipe 22, the covering portion 40 is attached to the first pipe 21 and the second pipe 22, and the second pipe 22 is attached to the operation portion 50.

Alternatively, the bent portions may also be formed after the first pipe 21 is attached to the second pipe 22 and the covering portion 40 is attached to the first pipe 21 and the second pipe 22 and before at least one of the attachment of the distal end electrode portion 10 to the first pipe 21 and the attachment of the second pipe 22 to the operation portion 50.

Specifically, the cautery puncture needle 1 has the first region a1 to the seventh region a7, and the bent portions are formed in the fourth region a4 and the sixth region a6. The first region a1 is a region in which the distal end electrode portion 10 is provided. The second region a2 is a region configured by a single layer that is the first pipe 21. The third region a3 is a region configured by two layers including the first pipe 21 and the second pipe 22, and is a linear region (a first linear portion) on a distal end side. The fourth region a4 is a region configured by two layers including the first pipe 21 and the second pipe 22, and is a bent region (a first bent portion). The fifth region a5 is a region configured by two layers including the first pipe 21 and the second pipe 22, and is a linear region (a second linear portion) on a proximal end side. The sixth region a6 is a region configured by a single layer that is the second pipe 22 and is a bent region (a second bent portion). The seventh region a7 is a region configured by a single layer that is the second pipe 22 and is a linear region (a third linear portion). The fifth region a5 is preferably implemented by two layers including the first pipe 21 and the second pipe 22, and may also be implemented by a single layer that is the second pipe 22 alone.

The first bent portion is located in a region configured by two layers including the first pipe 21 and the second pipe 22. The second bent portion is located in a region configured by a single layer that is the second pipe 22. That is, the pipe portion (the first pipe 21 and the second pipe 22) is configured such that the region implementing the first bent portion in the pipe portion is thicker than the region implementing the second bent portion in the pipe portion. Since the first bent portion is formed in the region configured by two layers including the first pipe 21 and the second pipe 22, a shape of the bent portion is easy to maintain as compared with the second bent portion formed in the region implemented by the single layer that is the second pipe 22. On the other hand, since the second bent portion is formed in the region configured by the single layer that is the second pipe 22, the second bent portion is easy to bend by an external force as compared with the first bent portion.

The two bent portions (the fourth region a4 and the sixth region a6) are bent in the same direction. The fourth region a4 and the sixth region a6 are configured such that a curvature radius R1 of an arc of the fourth region a4 is equal to or larger than a curvature radius R2 of an arc of the sixth region a6 and a length of the arc of the fourth region a4 is longer than a length of the arc of the sixth region a6. Specifically, relations of $R1 \geq R2$ (for example, $R1=R2=63.6$ mm) and the length of the arc of a4>the length of the arc of a6 (for example, the length of the arc of a4=34.6 mm and the length of the arc of a6=20.6 mm) are established. Alternatively, the fourth region a4 and the sixth region a6 are configured such that the length of the arc of the fourth region a4 is equal to or longer than the length of the arc of the sixth region a6 and the curvature radius R1 of the arc of the fourth region a4 is larger than the curvature radius R2 of the arc of the sixth region a6. That is, relations of the length of the arc of a4≥the length of the arc of a6 and $R1>R2$ are established. A difference in bending angle between the first bent portion and the second bent portion is preferably within a range of, for example, 5 degrees to 20 degrees.

The three linear portions (the third region a3, the fifth region a5, and the seventh region a7) extend in a substantially linear shape. Here, the "substantially linear shape" includes not only a shape extending in a straight line but also a shape gently curved with a curvature radius larger than the curvature radius R1 of the arc of the fourth region a4 and the curvature radius R2 of the sixth region a6.

(Effects of Providing Two Bent Portions Having Different Configurations)

The fourth region a4 and the sixth region a6 are configured such that the length of the arc is longer and/or the curvature radius is larger in the fourth region a4 than in the sixth region a6. For this reason, stress concentrates more in the sixth region a6 on the proximal end side than in other regions including the fourth region a4. The sixth region a6 (the second bent portion) is easy to bend as compared with other locations, and a user such as a doctor can easily and finely adjust the degree of bending. The fourth region a4 (the first bent portion) can easily maintain a bent state, and can be less likely to be bent unintendedly during surgery and the like.

The fourth region a4 (the first bent portion) is implemented by two layers including the first pipe 21 and the second pipe 22. The sixth region a6 (the second bent portion) is implemented by a single layer that is the second pipe 22. For this reason, the sixth region a6 is more easily bent than the fourth region a4, and a user such as a doctor can easily and finely adjust the degree of bending. The fourth region a4, which is less easily bent than the sixth region a6, easily maintains a bent state. For this reason, the fourth region a4 can be less likely to be bent unintendedly during surgery and the like.

(Effects of Surface Treatment for Entire Region of Region Covered by Covering Portion 40 such as Second Pipe 22)

The entire region of the first pipe 21 and the second pipe 22 that is covered with the covering portion 40 is subjected to a satin like surface treatment, so that the first pipe 21 and the like is in close contact with the covering portion 40, and wrinkles and the like are less likely to be generated in the covering portion 40. Accordingly, the cautery puncture needle 1 can be smoothly inserted into a sheath.

(Effects of Large Outer Diameter d1 of Distal End Electrode Portion 10)

By setting the outer diameter d1 of the distal end electrode portion 10 to be larger than the outer diameter d2 of the first pipe 21, an electrode surface area of the distal end electrode portion 10 can be large as compared with a configuration in which the outer diameter d1 is equal to the outer diameter d2 of the first pipe 21. With a large electrode surface area, electric cauterization can be performed stably and an intended location is easily punctured. A step between the distal end electrode portion 10 and the covering portion 40 is small, and thus the covering portion 40 is less likely to be in a peeled state or a rolled state.

(Effects of Providing Linear Portion Between Two Bent Portions)

The fifth region a5 (the second linear portion) is provided between the fourth region a4 (the first bent portion) and the sixth region a6 (the second bent portion). By providing the linear portion between the two bent portions, a position of a region to be bent by fine adjustment (the fourth region a4) is visually recognized easily. Further, since the fifth region a5 (the second linear portion) is configured by two layers including the first pipe 21 and the second pipe 22, the fifth region a5 is less likely to be bent than a region implemented by a single layer. For this reason, the fifth region a5 is easily maintained in a straight state, and can be less likely to be unintendedly bent during surgery and the like.

(Application Examples of Joining of First Pipe 21 and Second Pipe 22)

Figure 7:
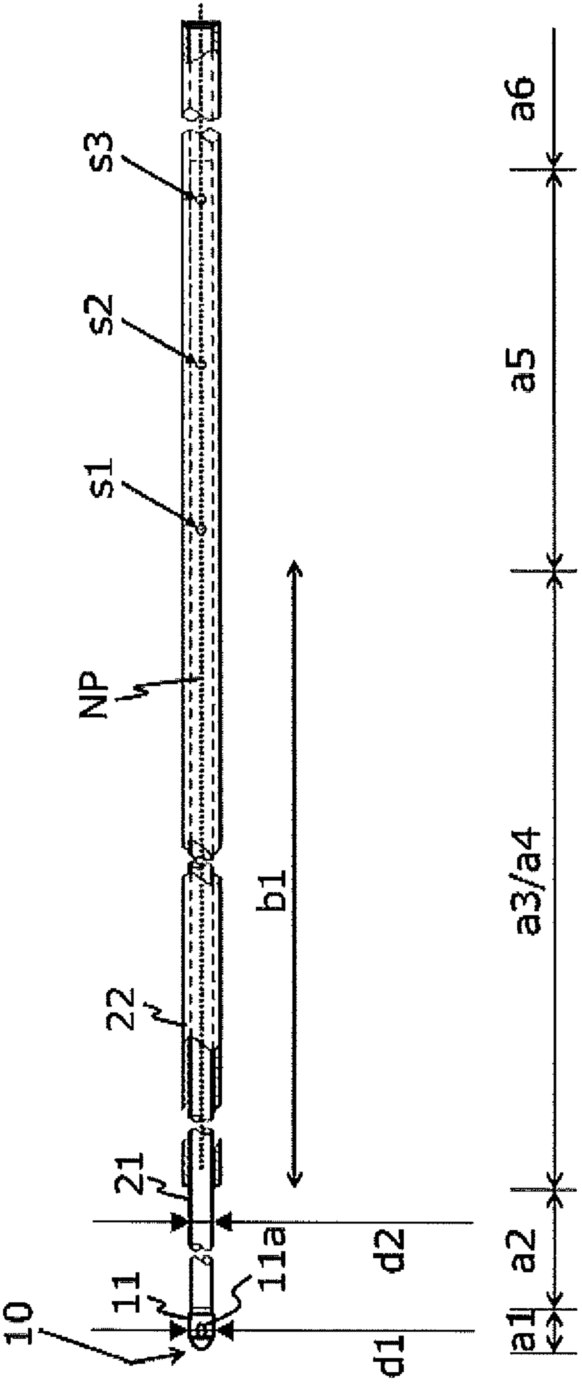
FIG. 7 shows side surfaces and partial cross sections of the distal end electrode portion, the first pipe, and the second pipe before being bent, and shows a joining example including both adhesion and spot welding.

The first pipe 21 and the second pipe 22 may be joined by both adhesion and welding. For example, as shown in FIG. 7, the first pipe 21 and the second pipe 21 are joined by adhesion on a distal end side (an adhesion region b1 that is a region including the third region a3 and the fourth region a4) and by spot welding on a proximal end side (the fifth region a5). The adhesion is performed for the purpose of, for example, preventing leakage of a contrast agent and the like. The spot welding is performed for the purpose of, for example, ensuring electrical conduction up to the distal end electrode portion 10, and preventing joint failure between the first pipe 21 and the second pipe 22. The spot welding is performed on a surface including a neutral plane NP of at least one of the first bent portion (the fourth region a4) and the second bent portion (the sixth region a6). FIG. 7 shows an example in which spot welding is performed at three locations s1, s2, and s3 in the fifth region a5 on the neutral plane NP. In this joining, adhesion on the distal end side is first performed, and then spot welding on the proximal end side is performed.

While certain embodiments are described, these embodiments are presented by way of examples only, and are not intended to limit the scope of the disclosure. These embodiments can be implemented by various other forms, and various omissions, replacements, and modifications can be made without departing from the gist of the disclosure. These embodiments and modifications thereof are included in the scope and the gist of the disclosure, and are included in a scope equivalent to the disclosure described in the claims.

According to the present specification, the following aspects are provided.

(Aspect 1)

A cautery puncture needle includes a pipe portion, and a distal end electrode portion provided at a distal end of the pipe portion and configured to allow a high-frequency current to flow. The pipe portion has a first bent portion and a second bent portion. The first bent portion is located on a distal end side of the pipe portion. The second bent portion is located on a proximal end side of the pipe portion. The first bent portion and the second bent portion are configured such that a curvature radius of an arc of the first bent portion is equal to or larger than a curvature radius of an arc of the second bent portion, and a length of the arc of the first bent portion is longer than a length of the arc of the second bent portion. Or, the first bent portion and the second bent portion are configured such that the length of the arc of the first bent portion equal to or longer than the length of the arc of the second bent portion, and the curvature radius of the arc of the first bent portion is larger than the curvature radius of the arc of the second bent portion.

According to Aspect 1, the first bent portion and the second bent portion are configured such that the first bent portion has a longer are and/or a larger curvature radius than the second bent portion. For this reason, stress concentrates on the second bent portion on the proximal end side more than in other regions including the first bent portion. The second bent portion is easy to bend as compared with other locations, and a user such as a doctor can easily and finely adjust the degree of bending. The first bent portion can easily maintain a bent state, and can be less likely to be bent unintendedly during surgery and the like.

(Aspect 2)

Preferably, the pipe portion includes a first pipe and a second pipe. The distal end electrode portion is provided on a distal end side of the first pipe. The first pipe has a proximal end side inserted into the second pipe. The first bent portion is located in a region of two layers including the first pipe and the second pipe. The second bent portion is located in a region of a single layer that is the second pipe.

According to Aspect 2, the second bent portion is easy to bend as compared with the first bent portion, and a user such as a doctor can easily and finely adjust the degree of bending. The first bent portion, which is less easily bent than the second bent portion, easily maintains a bent state. For this reason, the first bent portion can be less likely to be bent unintendedly during surgery and the like.

(Aspect 3)

More preferably, the cautery puncture needle further includes a covering portion covering the pipe portion. At least one of an outer side surface of the first pipe and an outer side surface of the second pipe is covered with the covering portion. An entire region covered with the covering portion is subjected to a satin like surface treatment.

According to Aspect 3, the entire region of the first pipe and the second pipe that is covered with the covering portion is subjected to a satin like surface treatment, so that the first pipe and the like is in close contact with the covering portion, and wrinkles and the like are less likely to be generated in the covering portion. Accordingly, the cautery puncture needle can be smoothly inserted into a sheath.

(Aspect 4)

More preferably, the distal end electrode portion has an outer diameter larger than an outer diameter of the first pipe and smaller than an outer diameter of a region of the covering portion that covers the first pipe.

According to Aspect 4, by setting the outer diameter of the distal end electrode portion to be larger than the outer diameter of the first pipe, an electrode surface area of the distal end electrode portion can be large as compared with a configuration in which the outer diameter is equal to the outer diameter of the first pipe. With a large electrode surface area, electric cauterization can be performed stably and an intended location is easily punctured. A step between the distal end electrode portion and the covering portion is small, and thus the covering portion is less likely to be in a peeled state or a rolled state.

(Aspect 5)

More preferably, the pipe portion has a linear portion between the first bent portion and the second bent portion. The linear portion is located in a region of two layers including the first pipe and the second pipe.

According to Aspect 5, by providing the linear portion between the two bent portions, a position of a region to be bent by fine adjustment (the second bent portion) is visually recognized easily. Further, since the linear portion is configured by two layers including the first pipe and the second pipe, the linear portion is less likely to be bent than a region implemented by a single layer. For this reason, the linear portion is easily maintained in a straight state, and can be less likely to be unintendedly bent during surgery and the like.

(Aspect 6)

More preferably, the first pipe and the second pipe are joined by adhesion on a distal end side and spot welding on a proximal end side.

According to Aspect 6, leakage of liquid passing through inside of the first pipe can be prevented by the adhesion on the distal end side. In addition, electrical conduction to the distal end electrode portion can be ensured by the spot welding on the proximal end side, and the first pipe and the second pipe can be hardly detached.

REFERENCE SIGNS LIST

1: cautery puncture needle
10: distal end electrode portion
11: tube portion
11*a*: hole
21: first pipe
21*a*: first hollow portion
22: second pipe
22*a*: second hollow portion
40: covering layer
50: operation portion
51: luer connecter
53: relay cable
55: syringe connection portion
a1: first region
a2: second region
a3: third region (first linear portion)
a4: fourth region (first bent portion)
a5: fifth region (second linear portion)
a6: sixth region (second bent portion)
a7: seventh region (third linear portion)
b1: adhesion region
d1: outer diameter of distal end electrode portion
d2: outer diameter of first pipe
d3: outer diameter of region of covering layer that covers first pipe
NP: neutral plane of at least one of first bent portion and second bent portion
s1 to s3: spot welding location

The invention claimed is:

1. A cautery puncture needle comprising:
a pipe portion; and
a distal end electrode portion provided at a distal end of the pipe portion and configured to allow a high-frequency current to flow, wherein:
the pipe portion has a first bent portion and a second bent portion,
the first bent portion is located on a distal end side of the pipe portion,
the second bent portion is located on a proximal end side of the pipe portion, and
the first bent portion and the second bent portion are configured such that a curvature radius of an arc of the first bent portion is equal to or larger than a curvature radius of an arc of the second bent portion and a length of the arc of the first bent portion is longer than a length of the arc of the second bent portion, or
the first bent portion and the second bent portion are configured such that the length of the arc of the first bent portion is equal to or longer than the length of the arc of the second bent portion and the curvature radius of the arc of the first bent portion is larger than the curvature radius of the arc of the second bent portion,
the pipe portion includes a first pipe and a second pipe,
the distal end electrode portion is provided on a distal end side of the first pipe,
the first pipe has a proximal end side inserted into the second pipe,
the first bent portion is located in a region of two layers including the first pipe and the second pipe, and
the second bent portion is located in a region of a single layer that is the second pipe.

2. The cautery puncture needle according to claim 1, further comprising:
a covering portion covering an outer side surface of the first pipe, wherein:
an entire region of the outer side surface of the first pipe covered with the covering portion is subjected to a satin-finished surface treatment.

3. The cautery puncture needle according to claim 2, wherein;
the distal end electrode portion has an outer diameter larger than an outer diameter of the first pipe and smaller than an outer diameter of a region of the covering portion that covers the first pipe.

4. The cautery puncture needle according to claim 3, wherein;
the pipe portion has a linear portion between the first bent portion and the second bent portion, and
the linear portion is located in the region of two layers including the first pipe and the second pipe.

5. The cautery puncture needle according to claim 4, wherein;
the first pipe and the second pipe are joined by adhesion on the distal end side of the pipe portion and spot welding on the proximal end side of the pipe portion.

6. The cautery puncture needle according to claim 3, wherein;
the first pipe and the second pipe are joined by adhesion on the distal end side of the pipe portion and spot welding on the proximal end side of the pipe portion.

7. The cautery puncture needle according to claim 3, wherein:
a distal end of the distal end electrode portion for insertion has a semi-elliptical spherical shape.

8. The cautery puncture needle according to claim 3, wherein:
the distal end electrode portion is provided with a tube portion communicating with the first pipe, and the tube portion is formed with a hole.

9. The cautery puncture needle according to claim 2, wherein:
the pipe portion has a linear portion between the first bent portion and the second bent portion, and
the linear portion is located in the region of two layers including the first pipe and the second pipe.

10. The cautery puncture needle according to claim 9, wherein:
the first pipe and the second pipe are joined by adhesion on the distal end side of the pipe portion and spot welding on the proximal end side of the pipe portion.

11. The cautery puncture needle according to claim 2, wherein:
the first pipe and the second pipe are joined by adhesion on the distal end side of the pipe portion and spot welding on the proximal end side of the pipe portion.

12. The cautery puncture needle according to claim 2, wherein:
a distal end of the distal end electrode portion for insertion has a semi-elliptical spherical shape.

13. The cautery puncture needle according to claim 2, wherein:
the distal end electrode portion is provided with a tube portion communicating with the first pipe, and the tube portion is formed with a hole.

14. The cautery puncture needle according to claim 2, wherein:

the first bent portion and the second bent portion are bent in a same direction.

15. The cautery puncture needle according to claim 1, wherein:

the pipe portion has a linear portion between the first bent portion and the second bent portion, and the linear portion is located in the region of two layers including the first pipe and the second pipe.

16. The cautery puncture needle according to claim 15, wherein;

the first pipe and the second pipe are joined by adhesion on the distal end side of the pipe portion and spot welding on the proximal end side of the pipe portion.

17. The cautery puncture needle according to claim 1, wherein:

the first pipe and the second pipe are joined by adhesion on the distal end side of the pipe portion and spot welding on the proximal end side of the pipe portion.

18. The cautery puncture needle according to claim 1, wherein:

a distal end of the distal end electrode portion for insertion has a semi-elliptical spherical shape.

19. The cautery puncture needle according to claim 1, wherein:

the distal end electrode portion is provided with a tube portion communicating with the first pipe, and the tube portion is formed with a hole.

20. The cautery puncture needle according to claim 1, wherein:

the first bent portion and the second bent portion are bent in a same direction.

* * * * *